US009809520B2

(12) United States Patent
Cheng et al.

(10) Patent No.: US 9,809,520 B2
(45) Date of Patent: Nov. 7, 2017

(54) BUTANOL PURIFICATION

(71) Applicant: Butamax Advanced Biofuels LLC, Wilmington, DE (US)

(72) Inventors: Cecilia Cheng, San Diego, CA (US); Ian David Dobson, London (GB); Andrew John Hogben, Leeds (GB); Andrew Richard Lucy, East Yorkshire (GB); John Glenn Sunley, East Yorkshire (GB); Leslie William Bolton, Hampshire (GB)

(73) Assignee: Butamax Advanced Biofuels LLC, Wilmington, DE (US)

( * ) Notice: Subject to any disclaimer, the term of this patent is extended or adjusted under 35 U.S.C. 154(b) by 177 days.

(21) Appl. No.: 14/416,510

(22) PCT Filed: Jul. 26, 2013

(86) PCT No.: PCT/US2013/052213
§ 371 (c)(1),
(2) Date: Jan. 22, 2015

(87) PCT Pub. No.: WO2014/018837
PCT Pub. Date: Jan. 30, 2014

(65) Prior Publication Data
US 2015/0225324 A1  Aug. 13, 2015

Related U.S. Application Data

(60) Provisional application No. 61/676,005, filed on Jul. 26, 2012.

(51) Int. Cl.
| C07C 29/88 | (2006.01) |
| C10L 1/18 | (2006.01) |
| C07C 29/80 | (2006.01) |
| C07C 29/76 | (2006.01) |
| C10L 1/02 | (2006.01) |
| C10L 1/182 | (2006.01) |
| C10L 1/14 | (2006.01) |
| C10L 1/185 | (2006.01) |
| C10L 1/188 | (2006.01) |

(52) U.S. Cl.
CPC ............ *C07C 29/88* (2013.01); *C07C 29/76* (2013.01); *C07C 29/80* (2013.01); *C10L 1/02* (2013.01); *C10L 1/023* (2013.01); *C10L 1/026* (2013.01); *C10L 1/18* (2013.01); *C10L 1/1824* (2013.01); *C10G 2400/02* (2013.01); *C10G 2400/04* (2013.01); *C10G 2400/08* (2013.01); *C10L 1/14* (2013.01); *C10L 1/1857* (2013.01); *C10L 1/1881* (2013.01); *C10L 2200/043* (2013.01); *C10L 2200/0423* (2013.01); *C10L 2200/0446* (2013.01); *C10L 2200/0469* (2013.01); *C10L 2270/023* (2013.01); *C10L 2270/026* (2013.01); *C10L 2270/04* (2013.01); *C10L 2290/26* (2013.01); *C10L 2290/54* (2013.01); *C10L 2290/543* (2013.01)

(58) Field of Classification Search
USPC ............................................ 44/411; 568/913
See application file for complete search history.

(56) References Cited

U.S. PATENT DOCUMENTS

| 3,111,381 | A | * | 11/1963 | Panzer | .................... C07C 51/41 |
| | | | | | 106/260 |
| 3,689,371 | A | * | 9/1972 | Kerber | ................... B01D 3/146 |
| | | | | | 203/18 |
| 6,117,277 | A | * | 9/2000 | Zgorzelski | .............. C07C 29/80 |
| | | | | | 203/37 |
| 8,373,008 | B2 | | 2/2013 | Grady et al. | |
| 8,373,009 | B2 | | 2/2013 | Grady et al. | |
| 8,409,834 | B2 | | 4/2013 | Burlew et al. | |
| 8,426,173 | B2 | | 4/2013 | Bramucci et al. | |
| 8,426,174 | B2 | | 4/2013 | Bramucci et al. | |
| 8,460,439 | B2 | | 6/2013 | Parten | |
| 8,476,047 | B2 | | 7/2013 | Burlew et al. | |
| 8,557,540 | B2 | | 10/2013 | Burlew et al. | |
| 8,563,788 | B2 | | 10/2013 | Grady et al. | |
| 8,569,552 | B2 | | 10/2013 | Grady et al. | |
| 8,574,406 | B2 | | 11/2013 | Grady et al. | |
| 8,617,861 | B2 | | 12/2013 | Grady et al. | |
| 8,628,643 | B2 | | 1/2014 | Grady et al. | |
| 8,697,404 | B2 | | 4/2014 | Anton et al. | |
| 8,759,044 | B2 | | 6/2014 | DiCosimo et al. | |
| 8,765,425 | B2 | | 7/2014 | DiCosimo et al. | |
| 8,828,695 | B2 | | 9/2014 | Grady et al. | |
| 8,865,443 | B2 | | 10/2014 | Burlew et al. | |
| 8,906,204 | B2 | | 12/2014 | Xu | |
| 8,968,522 | B2 | | 3/2015 | Xu et al. | |
| 8,968,523 | B2 | | 3/2015 | Xu et al. | |
| 8,969,055 | B2 | | 3/2015 | Grady et al. | |
| 9,012,190 | B2 | | 4/2015 | Dauner et al. | |
| 9,040,263 | B2 | | 5/2015 | Anton et al. | |
| 9,109,196 | B2 | | 8/2015 | Bazzana et al. | |
| 9,156,760 | B2 | | 10/2015 | Zaher et al. | |
| 9,175,315 | B2 | | 11/2015 | Anton et al. | |
| 9,206,448 | B2 | | 12/2015 | Anton et al. | |
| 9,249,076 | B2 | | 2/2016 | Anton et al. | |
| 9,371,547 | B2 | | 6/2016 | Burlew et al. | |
| 9,469,584 | B2 | | 10/2016 | Anton et al. | |
| 9,517,985 | B2 | | 12/2016 | Basham et al. | |
| 9,523,104 | B2 | | 12/2016 | Fuchs et al. | |

(Continued)

FOREIGN PATENT DOCUMENTS

EP         0110326      *  6/1984
WO    WO2009100848      8/2009

OTHER PUBLICATIONS

Wolf; EP0110326 Bib; published Jun. 1984.*

(Continued)

*Primary Examiner* — James Goloboy
*Assistant Examiner* — Chantel Graham

(57) ABSTRACT

Provided are methods for removing one or more components from a butanol based composition. The methods comprise providing a butanol based composition comprising one or more components, targeting at least one component or a combination thereof for reduction, and processing said butanol based composition such that the at least one targeted component is substantially removed. The butanol based composition can, for example, be bio-produced.

10 Claims, No Drawings

(56) References Cited

U.S. PATENT DOCUMENTS

| | | | |
|---|---|---|---|
| 2008/0182308 A1* | 7/2008 | Donaldson | C12N 9/0004 435/160 |
| 2008/0274526 A1 | 11/2008 | Bramucci et al. | |
| 2009/0199464 A1 | 8/2009 | Wolf | |
| 2009/0305370 A1 | 12/2009 | Grady et al. | |
| 2010/0143995 A1 | 6/2010 | Erdner-Tindall et al. | |
| 2010/0307053 A1 | 12/2010 | Kuberka et al. | |
| 2011/0023354 A1 | 2/2011 | Wolf | |
| 2011/0097773 A1 | 4/2011 | Grady et al. | |
| 2011/0136193 A1 | 6/2011 | Grady et al. | |
| 2011/0294179 A1 | 12/2011 | Grady et al. | |
| 2011/0312053 A1 | 12/2011 | Burlew et al. | |
| 2013/0164795 A1 | 6/2013 | Lowe et al. | |
| 2013/0217060 A1 | 8/2013 | Bramucci et al. | |
| 2013/0224728 A1 | 8/2013 | Bramucci et al. | |
| 2013/0252297 A1 | 9/2013 | Parten | |
| 2013/0295661 A1 | 11/2013 | Roesch et al. | |
| 2013/0309738 A1 | 11/2013 | Barr et al. | |
| 2014/0018581 A1 | 1/2014 | Grady et al. | |
| 2014/0024064 A1 | 1/2014 | Burlew et al. | |
| 2014/0073820 A1 | 3/2014 | Bazzana et al. | |
| 2014/0093931 A1 | 4/2014 | Dauner et al. | |
| 2014/0099688 A1 | 4/2014 | Grady et al. | |
| 2014/0106419 A1 | 4/2014 | Bazzana et al. | |
| 2014/0142352 A1 | 5/2014 | Dauner et al. | |
| 2014/0162344 A1 | 6/2014 | DiCosimo et al. | |
| 2014/0178529 A1 | 6/2014 | Anton et al. | |
| 2014/0234929 A1 | 8/2014 | Barr et al. | |
| 2014/0256020 A1 | 9/2014 | DiCosimo et al. | |
| 2014/0273130 A1 | 9/2014 | Anthony et al. | |
| 2014/0311889 A1 | 10/2014 | Zaher et al. | |
| 2014/0363865 A1 | 12/2014 | Burlew et al. | |
| 2015/0010984 A1 | 1/2015 | Bhalla et al. | |
| 2015/0060259 A1 | 3/2015 | Xu | |
| 2015/0080615 A1 | 3/2015 | Fergusson et al. | |
| 2015/0211026 A1 | 7/2015 | Bazzana et al. | |
| 2015/0267225 A1 | 9/2015 | Bazzana et al. | |

OTHER PUBLICATIONS

Wolf; EP0110326 Description Machine Translation; published Jun. 1984.*

International Search Report and Written Opinion for corresponding PCT/US2013/052213, dated Oct. 28, 2013.

International Preliminary Report on Patentability for corresponding PCT/US2013/052213, dated Jan. 27, 2015.

* cited by examiner

BUTANOL PURIFICATION

FIELD OF INVENTION

The present invention relates to methods for removing one or more components from a butanol based composition. The methods can, for example, comprise a neutralization step. The methods can, for example, further comprise a filtration step and/or a distillation step.

The present invention relates also to compositions comprising bio-produced butanol having reduced levels of certain deleterious bio-produced components and to fuel compositions comprising such butanol compositions.

BACKGROUND

Butanol is an important industrial chemical with a variety of applications, including use as a fuel additive, as a feedstock chemical in the plastics industry, and as a food-grade extractant in the food and flavor industry. Accordingly there is a high demand for butanol, as well as for efficient and environmentally friendly production methods. One such environmentally friendly production method includes the production of butanol utilizing fermentation by microorganisms. During the fermentation and subsequent purification steps, the butanol produced can comprise additional components that are deleterious in fuels prepared by blending the butanol with gasoline, one or more components of gasoline or other hydrocarbon-based fuels. These components can be, for example, one or more of isobutyric acid, isovaleric acid, and isobutyraldehyde. The methods provided herein can reduce the levels of these deleterious components in the butanol compositions produced by fermentation methods, thereby making the butanol more acceptable for end use applications to meet industry or end-user specifications.

The present invention satisfies the need to remove or eliminate additional components from bio-produced butanol based compositions by removing the one or more components from the butanol based compositions.

SUMMARY

Provided herein are methods for removing one or more components from a butanol based composition. The methods can, for example, comprise processing said butanol based composition such that at least one component is substantially removed. The methods can further comprise providing a butanol based composition comprising one or more components and targeting at least one component or a combination thereof for reduction. The one or more components can be, but are not limited to, a component selected from the group consisting of an acid, water, an alcohol, an aldehyde, a salt, a ketone, an ester, and combinations thereof.

Also provided herein are methods for removing one or more components from a butanol based composition. The methods can, for example, comprise providing a butanol based composition comprising one or more components, wherein the butanol based composition is produced by a genetically modified microorganism. The methods further comprise targeting at least one component or a combination thereof for reduction, and processing the butanol based composition such that at least one targeted component is substantially removed. The one or more components can be, but are not limited to, a component selected from the group consisting of an acid, water, an alcohol, an aldehyde, a salt, a ketone, an ester, and combinations thereof.

Further provided herein are methods for removing one or more components from a bio-produced butanol based composition. The methods can, for example, comprise providing a bio-produced butanol based composition comprising one or more components, targeting at least one component or a combination thereof for reduction, and processing the butanol based composition such that the at least one targeted component is substantially removed. The one or more components can be, but are not limited to, a component selected from the group consisting of an acid, water, an alcohol, an aldehyde, a salt, a ketone, an ester, and combinations thereof.

Optionally, the targeted component is an acid, and the processing step comprises contacting the butanol based composition with a base, a resin, or a combination thereof. The acid can be, but is not limited to, an acid selected from the group consisting of isobutyric acid, isovaleric acid, valeric acid, sulfuric acid, phosphoric acid, hydrochloric acid, formic acid, succinic acid, levulinic acid, lactic acid, acetic acid, butyric acid, and combinations thereof. Optionally, the base can be, but is not limited to, a base selected from the group consisting of calcium oxide, calcium hydroxide, sodium hydroxide, sodium carbonate, sodium phosphate, sodium ethoxide, potassium hydroxide, potassium carbonate, potassium phosphate, magnesium hydroxide, ammonium hydroxide, and combinations thereof. Contacting the butanol based composition with a base can, for example, result in the precipitation of a salt.

Optionally, the targeted component is water, and the processing step comprises contacting the butanol based composition with a desiccant, a molecular sieve, a base, or a combination thereof. The base can be, but is not limited to, a base selected from calcium oxide, calcium hydroxide, or a combination thereof.

Optionally, the targeted component is an alcohol, and the processing step comprises contacting the butanol based composition with a base. The alcohol can be, but is not limited to, an alcohol selected from the group consisting of ethanol, propanol, butanol, methyl butanol (e.g., 2-methyl butanol, 3-methyl butanol), phenyl ethyl alcohol, pentanol, 2,3-butanediol, and combinations thereof.

Optionally, the targeted component is an aldehyde, and the processing step comprises contacting the butanol based composition with a base, a resin, or a combination thereof. The aldehyde can be, but is not limited to, an aldehyde selected from the group consisting of isobutyraldehyde, furfural, hydroxymethylfurfural, and combinations thereof.

Optionally, the targeted component is a salt, and the processing step comprises contacting the butanol based composition with a base, an anion exchange resin, or a combination thereof.

Optionally, the targeted component is a ketone, and the processing step comprises contacting the butanol based composition with a base, a resin, or a combination thereof. The ketone can be, but is not limited to, acetoin.

Optionally, the targeted component is an ester and said processing step comprises contacting the butanol based composition with a base, a resin, or a combination thereof. The ester can be, but is not limited to, iso-butyl iso-butyrate, iso-butyl acetate, iso-amyl acetate, or a combination thereof, The methods can further comprise a filtration step. The filtration step can, for example, comprise passing the butanol based composition through a filtration system. Optionally, the filtration system comprises equipment selected from the group consisting of a funnel with a porous barrier, a sinter funnel, a vacuum filtration unit, a centrifugation unit, and combinations thereof.

The methods can further comprise a distillation step. The distillation step can, for example, comprise passing the filtered composition through a distillation system. The distillation system can comprise a distillation unit, wherein the distillation unit is selected from a batch distillation unit or a continuous distillation unit. The distillation unit can, for example, comprise a distillation column, a heating unit, and a condenser. Optionally, one or more distillation fractions comprising purified butanol are removed from the distillation system.

Further provided are methods of removing one or more components from a butanol based composition. The methods can, for example, comprise providing a butanol based composition comprising one or more components, contacting the butanol based composition with an excess level of a base, passing the composition through a filtration system, and passing the filtered composition through a distillation system. The one or more components can be, but are not limited to, a component selected from the group consisting of an acid, water, an alcohol, an aldehyde, a salt, a ketone, an ester, and combinations thereof. The one or more components can be, but are not limited to, a component selected from the group consisting of water, isobutyraldehyde, ethanol, iso-butyl acetate, propanol, iso-butyl iso-butyrate, iso-amyl acetate, butanol, methyl butanols, pentanol, acetoin, isobutyric acid, isovaleric acid, phenyl ethyl alcohol, 2,3-butanediol, valeric acid, sulfuric acid, phosphoric acid, hydrochloric acid, formic acid, succinic acid, levulinic acid, lactic acid, acetic acid, butyric acid, furfural, hydroxymethylfurfural, and combinations thereof.

Optionally, the base can be, but is not limited to, a base selected from the group consisting of calcium oxide, calcium hydroxide, sodium hydroxide, sodium carbonate, sodium phosphate, sodium ethoxide, potassium hydroxide, potassium carbonate, potassium phosphate, magnesium hydroxide, ammonium hydroxide, and combinations thereof. Contacting the butanol based composition with a base can, for example, result in the precipitation of a salt.

The methods can further comprise a filtration step. The filtration step can, for example, comprise passing the butanol based composition through a filtration system. Optionally, the filtration system comprises equipment that can be, but is not limited to, equipment selected from the group consisting of a funnel with a porous barrier, a sinter funnel, a vacuum filtration unit, a centrifugation unit, and combinations thereof.

The methods can further comprise a distillation step. The distillation step can, for example, comprise passing the filtered composition through a distillation system. The distillation system can comprise a distillation unit, wherein the distillation unit is selected from a batch distillation unit or a continuous distillation unit. The distillation unit can, for example, comprise a distillation column, a heating unit, and a condenser. Optionally, one or more distillation fractions comprising purified butanol are removed from the distillation system.

Optionally, the butanol based composition is a bio-produced butanol based composition. Optionally, the bio-produced butanol based composition is produced by a microorganism. The microorganism can, for example, be a genetically modified microorganism.

Also provided herein are compositions comprising bio-produced isobutanol and reduced levels of bio-produced isobutyric acid, for example, wherein the amount of bio-produced isobutyric acid is up to about 0.5, or up to about 0.01, or up to about 0.001 weight percent of the composition. Also provided herein are compositions comprising bio-produced isobutanol and less than about 0.5, or less than about 0.01, or less than about 0.001 weight percent bio-produced isobutyric acid. These compositions can comprise the product of treating a precursor composition comprising bio-produced isobutanol and bio-produced isobutyric acid by at least one process step or procedure to reduce the amount of isobutyric acid in the precursor composition. For example, the compositions comprising bio-produced isobutanol can be prepared by one or more of the methods disclosed in this application.

Also provided herein are compositions comprising bio-produced isobutanol and reduced levels of bio-produced isovaleric acid, for example, wherein the amount of bio-produced isovaleric acid is up to about 0.2 weight percent of the composition.

Also provided herein are compositions comprising bio-produced isobutanol and reduced levels of bio-produced isobutyraldehyde, for example, wherein the amount of bio-produced isobutyraldehyde is up to about 0.2 weight percent of the composition.

Also provided herein are fuel compositions comprising the aforementioned compositions and a hydrocarbon-containing fuel. These fuel compositions can be prepared, for example, by the method of combining one or more of the aforementioned compositions and a hydrocarbon-containing fuel. The hydrocarbon-containing fuel can comprise, for example, one or any combination of two or more of (a) a gasoline, (b) one or more components of gasoline, (c) a diesel fuel, (d) one or more components of diesel fuel, (e) jet fuel, and (f) one or more components of jet fuel. These fuel compositions can be prepared, for example, by the method of combining one or more of the aforementioned compositions and a hydrocarbon-containing fuel.

The fuel compositions can further comprise one or any combination of two or more of a corrosion inhibitor additive or additives, a metal deactivator additive or additives, a demulsifier additive or additives, a colorant additive or additives, a marker compound additive or additives, an intake valve deposit control additive or additives, a lubricant additive or additives, a detergent additive or additives, a dispersant additive or additives, an anti-oxidant additive or additives, a stabilizer additive or additives.

Also provided herein are methods for operating an internal combustion engine, such as an engine propelling an automobile, motorcycle, truck, boat or ship, airplane, jet plane, locomotive, or other vehicle, comprising combusting the aforementioned fuel compositions in the internal combustion engine.

DETAILED DESCRIPTION

In order to further define this invention, the following terms and definitions are herein provided.

As used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying the quantity of an ingredient or reactant of the invention employed refers to variation in the numerical quantity that can occur, for example, through typical measuring and liquid handling procedures used for making concentrates or solutions in the real world; through inadvertent error in these procedures; through differences in manufacture, source, or purity of the ingredients employed to make the compositions or to carry out the methods; and the like. The term "about" also encompasses amounts that differ due to different equilibrium conditions for a composition resulting from a particular initial mixture/composition. Whether or not modified by the term "about," the claims include equivalents to the quantities. In one embodiment, the term "about" means within 10% of the reported numerical value, alternatively, the term "about" means within 5% of the reported numerical value. Thus, the term "about" can mean within 1%, 2%, 3%, 4%, 5%, 6%, 7%, 8%, 9%, or 10% of the reported numerical value.

As used herein, the term "butanol based composition" means a composition, wherein the primary component of the composition is butanol. By primary component, it is meant that the component comprises greater than 50% of the composition. By way of an example, a butanol based composition can comprise a level of butanol between 50 and 99% of the composition, e.g., a level of butanol that is 51%, 55%, 60%, 65%, 70%, 75%, 80%, 85%, 90%, 95%, or 99% of the composition. A butanol based composition can comprise one or more components. The one or more components can be, but are not limited to, a component selected from the group consisting of an acid, water, an alcohol, an aldehyde, a salt, a ketone, an ester, and combinations thereof.

"Butanol," as used herein, refers to the butanol isomers 1-butanol (1-BuOH), 2-butanol (2-BuOH), tert-butanol (t-BuOH), and/or isobutanol (iBuOH or i-BuOH, also known as methyl-1-propanol), either individually or as mixtures thereof. From time to time, as used herein the terms "biobutanol" and "bio-produced butanol" may be used synonymously with "butanol."

Uses for butanol can include, but are not limited to, fuels (e.g., biofuels), a fuel additive, an alcohol used for the production of esters that can be used as diesel or biodiesel fuel, as a chemical in the plastics industry, an ingredient in formulated products such as cosmetics, and a chemical intermediate. Butanol may also be used as a solvent for paints, coatings, varnishes, resins, gums, dyes, fats, waxes, resins, shellac, rubbers, and alkaloids.

As used herein, the term "component" means a molecule or compound that can be in a butanol based composition. A component can be bio-derived. By bio-derived, it is meant that the component can be produced during a biological process (e.g., a fermentation process to produce the butanol). The bio-derived component can be subsequently distilled with the butanol after the biological process during a first distillation step. Alternatively, a component can be a molecule or compound added to a process to produce butanol (e.g., the component can be added to the fermentation medium during a fermentation process to aid in the production of butanol). The component can be subsequently distilled with the butanol after the biological process during a first distillation step. A component that is distilled concurrently with butanol during a first distillation step can be referred to as a codistillate. Removal of the one or more components to purify the butanol based composition can occur after the first distillation process. Alternatively, the one or more components can be removed prior to the first distillation process. Methods for the removal of the one or more components may comprise a second distillation step, which differs from the first distillation step at least in the timing of the distillation step (i.e., the second distillation step occurs after the first distillation step) and in the desired outcome of the distillation step (i.e., the second distillation step can result in the purification of the butanol, whereas the first distillation step can result in the extraction of the butanol composition from the fermentation medium).

As used herein, the term "bio-produced" means that the molecule (e.g., butanol) is produced from a renewable source (e.g., the molecule can be produced during a fermentation process from a renewable feedstock). Thus, for example, bio-produced isobutanol can be isobutanol produced by a fermentation process from a renewable feedstock. Molecules produced from a renewable source can further be defined by the 14C/12C isotope ratio. A 14C/12C isotope ratio in range of from 1:0 to greater than 0:1 indicates a bio-produced molecule, whereas a ratio of 0:1 indicates that the molecule is fossil derived.

As used herein, the term "fermentation medium" refers to the mixture of water, sugars, dissolved solids, optionally microorganisms producing alcohol, product alcohol (e.g., butanol), and all other constituents of the material in which product alcohol is being made by the reaction of sugars to alcohol, water, and carbon dioxide (CO2) by the microorganisms present. As used herein the term "fermentation broth" and "fermented mixture" can be used synonymously with "fermentation medium."

As used herein, the term "feedstock" refers to a feed in a fermentation process, the feed containing a fermentable carbon source with or without undissolved solids, and where and/or if applicable, the feed containing the fermentable carbon source before or after the fermentable carbon source has been liberated from starch or obtained from the breakdown of complex sugars by further processing.

As used herein, the term "genetically modified microorganism" refers to microorganisms such as bacteria or yeast, that are modified by use of recombinant DNA techniques, for example, by engineering a host cell to comprise a biosynthetic pathway such as a biosynthetic pathway to produce an alcohol such as butanol.

As used herein, the term "targeting" means the selective removal of enough component from the butanol based composition for the end use application of the butanol. Thus, the term "target" encompasses both the type of component and how much component should be removed for the end use application of the butanol. Targeting a specific component (e.g., an acid) can result in the removal of another component (e.g., an alcohol). Thus, while one component can be targeted for removal, it is understood that other components of the butanol based composition can be removed upon processing the targeted component. Therefore, the term "targeting" does not exclude components that are inadvertently removed.

Targeting requires processing the butanol based composition for the end use application of the butanol. Minimizing the processing of the butanol based composition and efficiently targeting the one or more components for removal can result in reducing costs to produce purified butanol.

For example, in an end use application of butanol as a fuel, the butanol composition can be about 96% pure, preferably about 98% pure, and most preferably about 99% pure. Acids, esters, and salts can be targeted for removal for fuel end use applications of purified butanol.

By way of another example, in an end use application of butanol for chemicals, the butanol should be about 99% pure, preferably about 99.5% pure, and most preferably about 99.9% pure. Acids, ketones, aldehydes, esters, salts, and water can be targeted for removal for chemical end use applications of purified butanol.

Provided herein are methods for removing one or more components from a butanol based composition. The methods comprise providing a butanol based composition comprising one or more components, targeting at least one component or a combination thereof for reduction, and processing the butanol based composition such that the at least one targeted component is substantially removed. Optionally, the butanol based composition is bio-produced. Optionally, the butanol based composition is produced by a genetically modified microorganism.

The one or more components can be, but are not limited to, a component selected from the group consisting of an acid, water, an alcohol, an aldehyde, a salt, a ketone, an ester, and combinations thereof. The one or more components are present due to the process of obtaining the butanol based composition. For example, the one or more components can be produced as byproducts in a fermentative process to produce butanol. Examples of components that can be produced as byproducts include, but are not limited to, alcohols other than butanol (e.g., ethanol, propanol, pentanol), aldehydes (e.g., isobutyraldehyde), water, ketones (e.g., acetoin), esters (e.g., iso-butyl iso-butyrate), and acids (e.g., isobutyric acid and isovaleric acid). By way of another example, the one or more components could be added to a fermentation broth used in a fermentation process to aid in the production of the butanol from the microorganism.

Removal of the one or more components is desired for the optimal end use application of the butanol. Butanol can, for example, be used in fuels (e.g., butanol can be blended with gasoline or other fuels). Acids, esters, and salts can be targeted for removal from the butanol based composition for fuel end use applications. Butanol can also, for example, be used in manufacture of chemicals (e.g., in the manufacture of lacquers and similar coatings; in the manufacture of plastics, rubbers, and other dispersions; in the manufacture of paint solvents; in the manufacture of inks; in the manufacture of paints; in the manufacture of automotive polishes). Acids, ketones, aldehydes, esters, salts, and water can be targeted for removal from the butanol based composition for chemical end use applications.

Identities and levels of the one or more components in a butanol based composition can, for example, be determined using methods selected from, but not limited to, gas chromatography (GC), gas chromatography-mass spectroscopy (GC-MS), mass spectroscopy (MS), high performance liquid chromatography (HPLC), nuclear magnetic resonance (NMR) spectroscopy, and near infrared (NIR) spectroscopy. These methods are known in the art. Briefly, by way of an example, the identity and level of the one or more components in a butanol based composition can be determined using gas chromatography. The butanol based composition can be compared to an internal standard using a gas chromatograph, which utilizes a capillary column and a flame ionization detector (FID) under temperature programmed conditions.

The butanol based composition can comprise an acid comprising about 5% of the weight of the composition. In certain embodiments, the acid is at a range of about 0.05 to about 5% of the weight of the composition. The acid can be at a range of about 0.1 to about 4.9%, about 0.5 to about 4.5%, about 1 to about 4%, about 1 to about 3%, about 1 to about 2%, about 2 to about 4%, about 2 to about 3%, about 3 to about 4%, or any value in between. An example of an acid can include, but are not limited to, isobutyric acid, valeric acid, isovaleric acid, sulfuric acid, phosphoric acid, hydrochloric acid, formic acid, succinic acid, levulinic acid, lactic acid, acetic acid, butyric acid, and combinations thereof.

The butanol based composition can comprise water at about 0.1% of the weight of the composition. In certain embodiments, the water is at a range of about 0.01 to about 1% of the weight of the composition. The water can, for example, be at a range of about 0.01 to about 1%, about 0.05 to about 0.95%, about 0.1 to about 0.9%, about 0.15 to about 0.85%, about 0.2 to about 0.8%, about 0.3 to about 0.7%, about 0.4 to about 0.6%, about 0.45 to about 0.55%, or any value in between.

The butanol based composition can comprise an alcohol comprising about 5% of the weight of the composition. In certain embodiments, the alcohol is at a range of about 0.05 to about 5% of the weight of the composition. The alcohol can be at a range of about 0.1 to about 4.9%, about 0.5 to about 4.5%, about 1 to about 4%, about 1 to about 3%, about 1 to about 2%, about 2 to about 4%, about 2 to about 3%, about 3 to about 4%, or any value in between. An example of an alcohol can include, but is not limited to, ethanol, propanol, 1-butanol, 2-butanol, 2-methyl butanol, 3-methyl butanol, phenyl ethyl alcohol, 1-pentanol, 2,3-butanediol, and combinations thereof.

The butanol based composition can comprise an aldehyde at about 0.001% of the weight of the composition. In certain embodiments, the aldehyde is at a range of about 0.001 to about 1% of the weight of the composition. The aldehyde can, for example, be at a range of about 0.001 to about 1%, about 0.002 to about 0.998%, about 0.005 to about 0.995%, about 0.010 to about 0.99%, about 0.020 to about 0.98%, about 0.05 to about 0.95%, about 0.1 to about 0.9%, about 0.2 to about 0.8%, or any value in between. An example of an aldehyde can include, but is not limited to, isobutyraldehyde, furfural, hydroxymethylfurfural, and combinations thereof.

The butanol based composition can comprise salt at about 1% of the weight of the composition. In certain embodiments, the salt is at a range of about 0.01 to about 1% of the weight of the composition. The salt can, for example, be at a range of about 0.01 to about 1%, 0.05 to about 0.95%, 0.1 to about 0.9%, 0.15 to about 0.85%, 0.2 to about 0.8%, 0.3 to about 0.7%, 0.4 to about 0.6%, 0.45 to about 0.55%, or any value in between.

The butanol based composition can comprise ketone at about 0.1% of the weight of the composition. In certain embodiments, the ketone is at a range of about 0.01 to about 1% of the weight of the composition. The ketone can, for example, be at a range of about 0.01 to about 1%, about 0.05 to about 0.95%, about 0.1 to about 0.9%, about 0.15 to about 0.85%, about 0.2 to about 0.8%, about 0.3 to about 0.7%, about 0.4 to about 0.6%, about 0.45 to about 0.55%, or any value in between. An example of a ketone can include, but is not limited to, acetoin.

The butanol based composition can comprise ester at about 1% of the weight of the composition. In certain embodiments, the ester is at a range of about 0.01 to about 1% of the weight of the composition. The ester can, for example, be at a range of about 0.01 to about 1%, 0.05 to about 0.95%, about 0.1 to about 0.9%, about 0.15 to about 0.85%, about 0.2 to about 0.8%, about 0.3 to about 0.7%, about 0.4 to about 0.6%, about 0.45 to 0.55%, or any value in between. An example of an ester can include, but is not limited to, iso-butyl iso-butyrate, iso-butyl acetate, iso-amyl acetate, or a combination thereof.

In one embodiment, the targeted component is an acid. To remove the acid, the butanol based composition can, for example, be contacted with a base, a resin, or a combination thereof. Contacting the butanol based composition with an excess of base can result in the neutralization of the acid and the precipitation of a salt. Methods of neutralizing acids from a composition by use of a base are known in the art, see, e.g., Chemistry: The Molecular Nature of Matter and Change, Martin Silberberg, McGraw-Hill, New York, N.Y. (2008); Organic Chemistry: An Acid-Base Approach, Michael Smith, CRC Press (2010); Sukhbaatar et al., Removal of acids from bio-oil, BioResources 4(4): 1319-1329 (2009); Wu et al., Efficient separation of butyric acid by an aqueous two-phase system with calcium chloride, Chinese Journal of Chemical Engineering 18(4):533-537 (2010). In certain embodiments, the butanol based composition comprising the precipitated salt can be passed through a filtration system or centrifuged to remove the salts. The filtered or centrifuged composition can further be passed through a distillation system to produce purified butanol. By way of another example, the butanol based composition can be contacted with a resin to remove the acid. Examples of resins that can be used to remove acids include, but not limited to, strong base anion-exchange resins and weak base anion exchange resins. Methods of using resins to remove acids from a composition are known in the art, see, e.g., Sukhbaatar et al., Removal of acids from bio-oil, BioResources 4(4):1319-1329 (2009); Anasthas and Gaikar, Reactive and Functional Polymers, 47(1):23-35 (2001). In certain embodiments, the targeted acids are removed from the butanol based composition by mixing the composition with resin in a vessel or by passing the butanol based composition through a column containing resin. The liquid fraction can then be passed through a distillation system to produce purified butanol.

In one embodiment, the targeted component is water. To remove the water, the butanol based composition can, for example, be contacted with a desiccant, a molecular sieve, a base, or a combination thereof. Methods of contacting compositions with a desiccant to remove water are known in the art, see, e.g., Burfield et al., J. Org Chem. 48:2420-2422 (1983); Burfield et al., J. Org Chem. 42(18):3060-3065 (1977). In certain embodiments, the desiccant is a chemical drying agent. Upon mixture of the drying agent with the butanol based composition, the desiccant and water can be removed from the butanol based composition by passing the composition through a filtration system. Optionally, the filtered composition is passed through a distillation system to produce purified butanol. By way of another example, the butanol based composition can be contacted with a molecular sieve to remove the water. The use of molecular sieves to remove water from compositions is known in the art, see, e.g., Williams and Lawton, J. Org. Chem. 75(24):8351-8354 (2010). By way of another example, the butanol based composition can be contacted with an excess of base to remove the water. Examples of bases that can be used to remove the water include, but are not limited to, calcium oxide and calcium hydroxide. Methods of using bases to remove water from a composition are known in the art, see, e.g., Zumdahl, Chemical Principles 6th Ed., Houghton Mifflin Company (2009); Breck, Crystalline molecular sieves, J. Chem. 41(12):678 (1964). In certain embodiments, the excess base and water can be removed from the butanol based composition by passing the composition through a filtration system followed by a distillation system to produce purified butanol.

In one embodiment, the targeted component is an alcohol other than butanol. To selectively remove the component alcohol, the butanol based composition can, for example, be contacted with a base. Optionally, the alcohol and base can be removed from the butanol based composition by passing the composition through a filtration system. In certain embodiments, the filtered composition can be passed through a distillation system to produce purified butanol. Optionally, the butanol can comprise substantially lower amounts of non-butanol based alcohols.

In one embodiment, the targeted component is an acetate. To remove the acetate, the butanol based composition can, for example, be contacted with a base, a resin, or a combination thereof. Methods of contacting a composition with a base to remove an acetate are known in the art, see, e.g., Chemistry: The Molecular Nature of Matter and Change, Martin Silberberg, McGraw-Hill, New York, N.Y. (2008). In certain embodiments, the acetate and excess base are removed from the butanol based composition by passing the composition through a filtration system. Optionally, the filtered composition is passed through a distillation system to produce purified butanol. By way of another example, the butanol based composition can be contacted with a resin to remove the acetate. Examples of resins that can be used to remove acetates include, but are not limited to, strong base anion-exchange resins and weak base anion-exchange resins. Methods of using resins to remove acetates from a composition are known in the art, see, e.g., Armarego and Chai, Purification of Laboratory Chemicals, Butterworth Heinemann (2009). In certain embodiments, the resin and targeted acetate are removed from the butanol based composition by passing the composition through a filtration system or by separating liquid fractions via centrifugation, followed by a distillation system to produce purified butanol.

In one embodiment, the targeted component is an aldehyde. To remove the aldehyde, the butanol based composition can, for example, be contacted with a base, a resin, or a combination thereof. Methods of using bases or resins for removing an aldehyde from a composition are known in the art, see, e.g., Armarego and Chai, Purification of Laboratory Chemicals, Butterworth Heinemann (2009). Examples of resins that can be used to remove aldehydes include, but are not limited to, strong base anion-exchange resins and weak base anion-exchange resins. In certain embodiments, the excess base, resin, and/or targeted aldehyde are removed from the butanol based composition by passing the composition through a filtration system, followed by a distillation system to produce purified butanol.

In one embodiment, the targeted component is a salt. To remove the salt, the butanol based composition can, for example, be contacted with a base, an anion exchange resin, or a combination thereof. Methods of using bases or resins for removing a salt from a composition are known in the art, see, e.g., van Raij et al., Communications in Soil Science and Plant Analysis. 17:547-566 (1986). In certain embodiments, the excess base, resin, and/or targeted salt are removed from the butanol based composition by passing the composition through a filtration system, followed by a distillation system to produce purified butanol.

In one embodiment, the targeted component is a ketone. To remove the ketone, the butanol based composition can, for example, be contacted with a base, a resin, or a combination thereof. Methods of using bases or resins for removing a ketone from a composition are known in the art, see, e.g., Armarego and Chai, Purification of Laboratory Chemicals, Butterworth Heinemann (2009). Examples of resins that can be used to remove ketones include, but are not limited to, strong base anion-exchange resins and weak base anion exchange resins. In certain embodiments, the excess base, resin, and/or targeted ketone are removed from the butanol based composition by passing the composition through a filtration system, followed by a distillation system to produce purified butanol.

In one embodiment, the targeted component is an ester. To remove the ester, the butanol based composition can, for example, be contacted with a base, a resin, or a combination thereof. Methods of using bases or resins for removing an ester from a composition are known in the art, see, e.g., Armarego and Chai, Purification of Laboratory Chemicals, Butterworth Heinemann (2009). Examples of resins that can be used to remove esters include, but are not limited to, strong base anion-exchange resins and weak base anion exchange resins. In certain embodiments, the excess base, resin, and/or targeted ester are removed from the butanol based composition by passing the composition through a filtration system, followed by a distillation system to produce purified butanol.

Examples of bases to be used in the methods described can include, but are not limited to, calcium oxide, calcium hydroxide, sodium hydroxide, sodium carbonate, sodium phosphate, sodium ethoxide, potassium hydroxide, potassium carbonate, potassium phosphate, magnesium hydroxide, ammonium hydroxide, and combinations thereof.

Optionally, the methods of removing one or more components from a butanol based composition can further comprise a filtration step. The filtration step can comprise passing the butanol based composition through a filtration system. By way of an example, a filtration system can comprise equipment selected from the group consisting of a funnel with a porous barrier, a sinter funnel, a vacuum filtration unit, a centrifugation unit, and combinations thereof. Filtration systems are known in the art. See, e.g., Filters and Filtration Handbook, 4th Ed., T. C. Dickerson (1998).

Optionally, the methods of removing one or more components from a butanol based composition can further comprise a second distillation step. The distillation step can comprise passing the filtered butanol based composition through a distillation system. A distillation system can, for example, comprise a distillation unit, wherein the distillation unit is selected from a batch distillation unit or a continuous distillation unit. Optionally, the distillation unit comprises a distillation column, a heating unit, and a condenser. During the distillation step, one or more fractions comprising purified butanol are removed from the distillation system. Distillation systems are known in the art, see, e.g., Armarego and Chai, Purification of Laboratory Chemicals, Butterworth Heinemann (2009).

Embodiments of the invention include compositions comprising bio-produced isobutanol and bio-produced isobutyric acid. The compositions comprising bio-produced isobutanol and bio-produced isobutyric acid can also comprise bio-produced isovaleric acid. The compositions comprising bio-produced isobutanol and bio-produced isobutyric acid can also comprise bio-produced isobutyraldehyde. These compositions comprising bio-produced isobutanol, bio-produced isobutyric acid and bio-produced isovaleric acid can also comprise bio-produced isobutyraldehyde. Embodiments include compositions comprising bio-produced isobutanol and bio-produced isovaleric acid, compositions comprising bio-produced isobutanol and bio-produced isobutyraldehyde, and compositions comprising bio-produced isobutanol, bio-produced isovaleric acid, and bio-produced isobutyraldehyde.

In certain embodiments, the amount of bio-produced isobutyric acid in compositions comprising bio-produced isobutyric acid can be up to about 1.0 weight percent of the composition, for example, up to about 0.9, 0.8, 0.7, 0.6, 0.5, 0.4, 0.3, 0.25 or 0.2 weight percent of the composition. The compositions comprising bio-produced isobutyric acid can comprise an amount of bio-produced isobutyric acid that is up to about 0.1 weight percent of the composition, for example, up to about 0.075, 0.05, 0.025, 0.02, or 0.01 weight percent of the composition. The compositions comprising bio-produced isobutyric acid can comprise an amount of bio-produced isobutyric acid that is up to about 0.0075 weight percent of the composition, for example, up to about 0.005, 0.0025, 0.002, or 0.001 weight percent of the composition. The compositions comprising bio-produced isobutyric acid can comprise an amount of bio-produced isobutyric acid that is up to about 0.00075 weight percent of the composition, for example, up to about 0.0005, 0.00025, 0.0002, or 0.0001 weight percent of the composition.

In certain embodiments, the amount of bio-produced isovaleric acid in compositions comprising bio-produced isovaleric acid can be up to about 0.2 weight percent of the composition. The amount of isovaleric acid in these compositions can be up to about 0.1 weight percent of the composition, or up to about 0.05, or up to about 0.01 weight percent of the composition.

In certain embodiments, the amount of bio-produced isobutyraldehyde in compositions comprising bio-produced isobutyraldehyde can be up to about 0.2 weight percent of the composition. The amount of isobutyraldehyde in these compositions can be up to about 0.1 weight percent of the composition, or up to about 0.05, or up to about 0.01 weight percent of the composition.

In certain embodiments, the amount of bio-produced isobutyric acid in compositions comprising bio-produced isobutyric acid can be at least about 0.0001 weight percent of the composition. For example, in compositions where the amount of bio-produced isobutyric acid can be up to about 1.0 or up to about 0.001 weight percent, the amount of bio-produced isobutyric acid can be at least about 0.001 weight percent of the composition. In compositions where the amount of bio-produced isobutyric acid can be up to about 1.0 or about up to about 0.005 weight percent, the amount of bio-produced isobutyric acid can be at least about 0.005 weight percent of the composition. In compositions where the amount of bio-produced isobutyric acid can be up to about 1.0 or up to about 0.01 weight percent, the amount of bio-produced isobutyric acid can be at least about 0.01 weight percent of the composition.

In certain embodiments, the amount of bio-produced isovaleric acid in compositions comprising bio-produced isovaleric acid can be at least about 0.0001 weight percent of the composition. For example, the amount of bio-produced isovaleric acid can be at least about 0.001, 0.005, or 0.01 weight percent of the composition.

In certain embodiments, the amount of bio-produced isobutyraldehyde in compositions comprising bio-produced isobutyraldehyde can be at least about 0.0001 weight percent of the composition. For example, the amount of bio-produced isobutyraldehyde acid can be at least about 0.001, 0.005 or 0.01 weight percent of the composition.

Any combination of the various amounts of bio-produced isobutyric acid, bio-produced isovaleric acid and bio-produced isobutyraldehyde stated above is included as an embodiment herein. For example, the compositions comprising bio-produced isobutanol can include a composition wherein the amount of bio-produced isobutyric acid is up to about 0.1 weight percent, the amount of bio-produced isovaleric acid is up to about 0.05 weight percent and the amount of bio-produced isobutyraldehyde is up to about 0.01 weight percent of the composition. As another example, the compositions comprising bio-produced isobutanol can include a composition wherein the amount of bio-produced isobutyric acid is up to about 0.1 weight percent and at least about 0.001 weight percent, the amount of bio-produced isovaleric acid is up to about 0.01 weight percent and at least about 0.005 and the amount of bio-produced isobutyraldehyde is up to about 0.05 weight percent and at least about 0.005 weight percent of the composition.

For the compositions described as comprising bio-produced isobutanol and bio-produced isobutyric acid, the amount of bio-produced isobutyric acid can be up to about "X" weight percent of the composition and at least about "A" weight percent, where X, independently of A, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, and A, independently of X, can be 0.0001, 0.001, 0.005 or 0.01, except that for any given composition, the value of A cannot be greater than the value of X.

For the compositions described as comprising bio-produced isobutanol and bio-produced isovaleric acid, the amount of isovaleric acid can be up to about "Y" weight percent of the composition and at least about "B" weight percent, where Y, independently of B, can be 0.2, 0.1, 0.05 or 0.01, and B independently of Y, can be 0.0001, 0.001, 0.005 or 0.01, except that for any given composition, the value of B cannot be greater than the value of Y.

For the compositions described as comprising bio-produced isobutanol and bio-produced isobutyraldehyde, the amount of bio-produced isobutyraldehyde can be up to about "Z" weight percent of the composition and at least about "C" weight percent, where Z, independently of C, can be 0.2, 0.1, 0.05 or 0.01, and C, independently of Z, can be 0.0001, 0.001, 0.005 or 0.01, except that for any given composition, the value of C cannot be greater than the value of Z.

For the compositions described as comprising bio-produced isobutanol, bio-produced isobutyric acid, and bio-produced isovaleric acid, the amount of bio-produced isobutyric acid can. be up to about "X" weight percent of the composition, and the amount of bio-produced isovaleric acid can be up to about "Y" weight percent of the composition, where X, independently of Y, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, and Y, independently of X, can be 0.2, 0.1, 0.05 or 0.01.

For the compositions described as comprising bio-produced isobutanol, bio-produced isobutyric acid, and bio-produced isovaleric acid, the amount of bio-produced isobutyric acid can be up to about "X" weight percent of the composition and at least about "A" weight percent of the composition, the amount of bio-produced isovaleric acid can be up to about "Y" weight percent of the composition and at least about "B" weight percent of the composition, where X, independently of Y, A and B, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, Y, independently of X, A and B, can be 0.2, 0.1, 0.05 or 0.01, A, independently of X, Y and B, can be 0.0001, 0.001, 0.005 or 0.01 (except that for any given composition, the value of A cannot be greater than the value of X), and B, independently of X, Y, and A, can be 0.0001, 0.001, 0.005 or 0.01 (except that for any given composition, the value of B cannot be greater than the value of Y).

For the compositions described as comprising bio-produced isobutanol, bio-produced isobutyric acid, and bio-produced isobutyraldehyde, the amount of bio-produced isobutyric acid can be up to about "X" weight percent of the composition and the amount of bio-produced isobutyraldehyde can be up to about "Z" weight percent of the composition where X, independently of Z, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, and Z, independently of X, can be 0.2, 0.1, 0.05 or 0.01.

For the compositions described as comprising bio-produced isobutanol, bio-produced isobutyric acid, and bio-produced isobutyraldehyde, the amount of bio-produced isobutyric acid can be up to about "X" weight percent of the composition and at least about "A" weight percent of the composition, and the amount of bio-produced isobutyraldehyde can be up to about "Z" weight percent of the composition and at least about "C" weight percent of the composition, where X, independently of Z, A and C, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, Z, independently of X, A and C, can be 02, 0.1, 0.05 or 0.01, A, independently of X, Y and B, can be 0.0001, 0.001, 0.005 or 0.01 (except that for any given composition, the value of A cannot be greater than the value of X), and C, independently of X, Z and A, can be 0.0001, 0.001, 0.005 or 0.01 (except that for any given composition, the value of C cannot be greater than the value of Z).

For the compositions comprising bio-produced isobutanol, bio-produced isovaleric acid, and bio-produced isobutyraldehyde, the amount of bio-produced isovaleric acid can be up to about "Y" weight percent of the composition, and the amount of bio-produced isobutyraldehyde can be up to about "Z" weight percent of the composition where Y, independently of Z, can be 0.2, 0.1, 0.05 or 0.01, and Z, independently of Y, can be 0.2, 0.1, 0.05 or 0.01.

For the compositions comprising bio-produced isobutanol, bio-produced isovaleric acid and bio-produced isobutyraldehyde, the amount of bio-produced isovaleric acid can be up to about "Y" weight percent of the composition and at least about "B" weight percent of the composition, and the amount of bio-produced isobutyraldehyde can be up to about "Z" weight percent of the composition and at least about "C" weight percent of the composition, where Y, independently of Z, B, and C, can be 0.2, 0.1, 0.05 or 0.01, Z, independently of Y, B and C, can be 0.2, 0.1, 0.05 or 0.01, B, independently of Y, Z, and C, can be 0.0001, 0.001, 0.005 or 0.01 (except that for any given composition, the value of B cannot be greater than the value of Y), and C, independently of Y, Z, and B, can be 0.0001, 0.001, 0.005 or 0.01 (except that for any given composition, the value of C cannot be greater than the value of Z).

For the compositions comprising bio-produced isobutanol, bio-produced isobutyric acid, bio-produced isovaleric acid, and bio-produced isobutyraldehyde, the amount of bio-produced isobutyric acid can be up to about "X" weight percent of the composition, the amount of bio-produced isovaleric acid can be up to about "Y" weight percent of the composition, and the amount of bio-produced isobutyraldehyde can be up to about "Z" weight percent of the composition where X, independently of Y and Z, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, Y, independently of X and Z, can be 0.2, 0.1, 0.05 or 0.01, and Z, independently of X and Y, can be 0.2, 0.1, 0.05 or 0.01.

For the compositions comprising bio-produced isobutanol, bio-produced isobutyric acid, bio-produced isovaleric acid and bio-produced isobutyraldehyde, the amount of bio-produced isobutyric acid can be up to about "X" weight percent of the composition and at least about "A" weight percent of the composition, the amount of bio-produced isovaleric acid can be up to about "Y" weight percent of the composition and at least about "B" weight percent of the composition, and the amount of bio-produced isobutyraldehyde can be up to about "Z" weight percent of the composition and at least about "C" weight percent of the composition, where X, independently of Y, Z, A, B and C, can be 1.0, 0.9, 0.8, 0.7, 0.6, 0.5, 0.4, 0.3, 0.25, 0.20, 0.01, 0.075, 0.05, 0.025, 0.02, 0.01, 0.0075, 0.005, 0.0025, 0.002, 0.001, 0.00075, 0.0005, 0.00025, 0.0002, or 0.0001, Y, independently of X, Z, A, B, and C, can be 0.2, 0.1, 0.05 or 0.01, Z, independently of X, Y, A, B and C, can be 0.2, 0.1, 0.05 or 0.01, A, independently of X, Y, Z, B and C, can be 0.0001, 0.001, 0.005 or 0.01 (except that for any given composition, the value of A cannot be greater than the value of X), B, independently of X, Y, Z, A and C can be 0.0001, 0.001, 0.005 or 0.01 (except that for any given composition, the value of B cannot be greater than the value of Y), and C independently of X, Y, Z, A and B can be 0.0001, 0.001, 0.005 or 0.01 (except that for any given composition, the value of C cannot be greater than the value of Z).

Alternatively, the composition comprising bio-produced isobutanol can comprise less than about 1.0 weight percent bio-produced isobutyric acid, for example, less than about 0.9, 0.8, 0.7, 0.6, 0.5, 0.4, 0.3 or 0.2 weight percent bio-produced isobutyric acid. The composition comprising bio-produced isobutanol can comprise less than about 0.1 weight percent bio-produced isobutyric acid, for example, less than about 0.075, 0.05, 0.025, 0.02, or 0.01 weight percent bio-produced isobutyric acid. The composition comprising bio-produced isobutanol can comprise less than about 0.0075 weight percent bio-produced isobutyric acid, for example, less than about 0.005, 0.05, 0.0025, 0.002, or 0.001 weight percent bio-produced isobutyric acid. The composition comprising bio-produced isobutanol can comprise less than about 0.00075 weight percent bio-produced isobutyric acid, for example, less than about 0.00050, 0.00025, 0.0002, or 0.0001 weight percent bio-produced isobutyric acid. In these alternatively described compositions comprising bio-produced isobutanol, the compositions can comprise less than about 0.01 weight percent isovaleric acid. The compositions can comprise less than about 0.01 weight percent isobutyraldehyde. The compositions can comprise less than about 0.01 weight percent isovaleric acid and less than about 0.01 weight percent isobutyraldehyde.

For any of these compositions described above comprising bio-produced isobutanol, the amount of the bio-produced isobutanol can be at least about 50 weight percent of the composition, or at least about 55 weight percent of the composition, or at least about 60 weight percent of the composition, or at least about 65 weight percent of the composition, or at least about 70 weight percent of the composition, or at least about 75 weight percent of the composition, or at least about 80 weight percent of the composition, or at least about 85 weight percent of the composition, or at least about 90 weight percent of the composition, or at least about 95 weight percent of the composition, or at least about 98 weight percent of the composition, or at least about 99 weight percent of the composition.

For any of these compositions described above comprising bio-produced isobutanol, the composition can be the product of treating a precursor composition comprising bio-produced isobutanol and bio-produced isobutyric acid by at least one process step to reduce the amount of bio-produced isobutyric acid in the precursor composition. For example, the process step can comprise treating the precursor composition with a base, or a resin, or a combination thereof. Such treating can be in the manner as disclosed herein for processing an isobutanol based composition.

The compositions comprising bio-produced isobutanol described above can have a mass that is at least about 100 kilograms, or at least about 500 kilograms, or at least about 1000 kilograms. They can have a mass that is at least about 5000 or about 10000 kilograms.

Embodiments also include fuel compositions comprising any of the compositions described above comprising bio-produced isobutanol and comprising a hydrocarbon-containing fuel. In certain embodiments, the hydrocarbon-containing fuel is gasoline or one or more ingredients or components of gasoline. As used herein the terms "ingredients of gasoline" or "components of gasoline" mean one or more of the hydrocarbon-containing ingredients or components used to manufacture gasoline. Ingredients or components of gasoline can include, for example, alkylate, reformate (e.g., light reformate and heavy reformate), isomerate, naphtha (e.g., light naphtha, light virgin naphtha, heavy naphtha, light FCC naphtha and heavy FCC naphtha ("FCC" is a fluidized bed catalytic cracker), and coker naphtha, such as light coker naphtha and heavy coker naphtha), butane and toluene. Gasoline can also have as an ingredient or component one or more oxygenated compounds such as ethanol or an ether such as, for example, tertiary amyl methyl ether (TAME), ethyl tert-butyl ether (ETBE) and methyl tert-butyl ether (MTBE). These ingredients or components can be used in amounts to meet specifications, for example, regional specifications, or desired performance properties for a fuel. For example, gasoline containing isobutanol can have higher levels of light naphtha and other compounds having relatively high vapor pressure, such as pentanes and butanes. In certain embodiments, the hydrocarbon-containing fuel is diesel fuel or one or more ingredients or components of diesel fuel. As used herein the terms "ingredients of diesel fuel" or "components of diesel fuel" mean one or more of the hydrocarbon-containing ingredients or components used to manufacture diesel fuel. Ingredients or components of diesel fuel can include, for example, light middle distillate and heavy middle distillate, FCC light catalytic cycle oil, and coker distillate. One or all of these distillates can be hydrotreated to, for example, reduce the amount of sulfur. In certain embodiments, the hydrocarbon-containing fuel is jet fuel or one or more ingredients or components of jet fuel. As used herein the terms "ingredients of jet fuel" or "components of jet fuel" mean one or more of the hydrocarbon-containing ingredients or components used to manufacture jet fuel. Ingredients or components of jet fuel can include, for example, light middle distillate. Certain jet fuels can contain heavy naphtha.

The fuel composition can comprise one or more additives that, for example, can improve the performance of the fuel composition. For example, the fuel compositions can comprise one or any combination of two or more of a corrosion inhibitor additive or additives, a metal deactivator additive or additives, a demulsifier additive or additives, a colorant additive or additives, a marker compound additive or additives, a lubricant additive or additives, a detergent additive or additives, an intake valve deposit control additive, or additives, a dispersant additive or additives, an anti-oxidant additive or additives, a stabilizer additive or additives. The fuel compositions can have an amount of one or more of these additives to achieve a desired performance. For example, each additive can be added so there is about 1 to about 10000 parts per million by weight (PPMW), for example, 1 to about 1000, or 1 to about 100 PPMW, of the additive in the fuel composition. The United States Environmental Protection Agency lists registered fuel additives in the United States Environmental Protection Agency's listing "List of Registered Fuels and Fuel Additives," and in particular such listing that is current as of Jun. 18, 2012.

In these fuel compositions comprising bio-produced isobutanol and a hydrocarbon-containing fuel, the amount of the bio-produced isobutanol composition can be about 1 to about 99 volume percent of the fuel composition, about 1 to about 95 volume percent of the fuel composition, about 5 to about 95 volume percent of the fuel composition, about 5 to about 75 volume percent of the fuel composition, about 5 to about 50 volume percent of the fuel composition, about 5 to about 40 volume percent of the fuel composition, about 5 to about 30 volume percent of the fuel composition, about 5 to about 20 volume percent of the fuel composition, about 5 to about 10 volume percent of the fuel composition, about 15 to about 25 volume percent of the fuel composition, about 16 to about 24 volume percent of the fuel composition, about 16 volume percent of the fuel composition, about 24 volume percent of the fuel composition.

These fuel compositions can be prepared by combining the composition comprising the bio-produced isobutanol with the hydrocarbon-containing fuel. The bio-produced isobutanol and the hydrocarbon-containing fuel can be combined, for example, at an oil refinery where, for example, the hydrocarbon-containing fuel is manufactured or they can be combined at a location away from a refinery such as, for example, at a fuel blending facility used to supply automotive and other vehicle fuel to local markets. These bio-produced isobutanol and hydrocarbon-containing fuels have more renewable carbon than other fuel blends and surprising little other components typically produced by fermentation production of alcohols by virtue of the purification steps provided herein.

Recombinant Microorganisms

While not wishing to be bound by theory, it is believed that the bio-produced butanol based compositions described herein can be produced by any butanol producing microorganism, particularly, genetically modified microorganisms that produce butanol.

For example, the metabolic pathways of microorganisms may be genetically modified to produce butanol. These pathways may also be modified to reduce or eliminate undesired metabolites, and thereby improve the yield of the butanol. The microorganisms may also be modified to reduce or eliminate byproducts which may codistill with the butanol after production of the butanol by the microorganism. The production of butanol by a microorganism is disclosed, for example, in U.S. Pat. Nos. 7,851,188; 7,993,889; 8,178,328, 8,206,970; U.S. Patent Application Publication Nos. 2007/0292927; 2008/0182308; 2008/0274525; 2009/0305363; 2009/0305370; 2011/0250610; 2011/0313206; and 2011/0111472. In some embodiments, microorganisms comprise a biosynthetic pathway for butanol. In some embodiments, the microorganism may be bacteria, cyanobacteria, filamentous fungi, or yeasts. Suitable microorganisms capable of producing isobutanol via a biosynthetic pathway include, but are not limited to, a member of the genera *Clostridium, Zymomonas, Escherichia, Salmonella, Serratia, Erwinia, Klebsiella, Shigella, Rhodococcus, Pseudomonas, Bacillus, Lactobacillus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma,* or *Saccharomyces*. In one embodiment, recombinant microorganisms may be selected from the group consisting of *Escherichia coli, Alcaligenes eutrophus, Bacillus licheniformis, Paenibacillus macerans, Rhodocuccus erythropolis, Pseudomonas putida, Lactobacillus plantarum, Enterococcus faecium, Enterococcus gallinarium, Enterococcus faecalis, Bacillus subtilis, Candida sonorensis, Candida methanosorbosa, Kluyveromyces lactis, Kluyveromyces marxianus, Kluveromyces thermotolerans, Issatchenkia orientalis, Debaryomyces hansenii,* and *Saccharomyces cerevisiae*. In one embodiment, the genetically modified microorganism is yeast. In one embodiment, the genetically modified microorganism is a crabtree-positive yeast selected from *Saccharomyces, Zygosaccharomyces, Schizosaccharomyces, Dekkera, Torulopsis, Brettanomyces,* and some species of *Candida*. Species of crabtree-positive yeast include, but are not limited to, *Saccharomyces cerevisiae, Saccharomyces kluyveri, Schizosaccharomyces pombe, Saccharomyces bayanus, Saccharomyces mikitae, Saccharomyces paradoxus, Saccharomyces uvarum, Saccharomyces castelli, Zygosaccharomyces rouxii, Zygosaccharomyces bailli,* and *Candida glabrata*.

In some embodiments, the host cell is *Saccharomyces cerevisiae*. *Saccharomyces cerevisiae* are known in the art and are available from a variety of sources including, but not limited to, American Type Culture Collection (Rockville, Md.), Centraalbureau voor Schimmelcultures (CBS) Fungal Biodiversity Centre, LeSaffre, Gert Strand AB, Ferm Solutions, North American Bioproducts, Martrex, and Lallemand. *S. cerevisiae* include, but are not limited to, BY474I, CEN.PK 113-7D, Ethanol Red® yeast, Ferm Pro™ yeast, Bio-Ferm® XR yeast, Gert Strand Prestige Batch Turbo alcohol yeast, Gert Strand Pot Distillers yeast, Gert Strand Distillers Turbo yeast, FerMax™ Green yeast, FerMax™ Gold yeast, Thermosacc® yeast, BG-1, PE-2, CAT-1, CBS7959, CBS7960, and CBS7961.

In some embodiments, the microorganism may be immobilized or encapsulated. For example, the microorganism may be immobilized or encapsulated using alginate, calcium alginate, or polyacrylamide gels, or through the induction of biofilm formation onto a variety of high surface area support matrices such as diatomite, celite, diatomaceous earth, silica gels, plastics, or resins. In some embodiments, ISPR may be used in combination with immobilized or encapsulated microorganisms. This combination may improve productivity such as specific volumetric productivity, metabolic rate, product alcohol yields, and tolerance to product alcohol. In addition, immobilization and encapsulation may minimize the effects of the process conditions such as shearing on the microorganisms.

Biosynthetic pathways for the production of isobutanol that may be used include those as described by Donaldson et al. in U.S. Pat. No. 7,851,188; U.S. Pat. No. 7,993,388; and International Publication No. WO 2007/050671. In one embodiment, the isobutanol biosynthetic pathway comprises the following substrate to product conversions:
  a) pyruvate to acetolactate, which may be catalyzed, for example, by acetolactate synthase;
  b) the acetolactate from step a) to 2,3-dihydroxyisovalerate, which may be catalyzed, for example, by acetohydroxy acid reductoisomerase;
  c) the 2,3-dihydroxyisovalerate from step b) to α-ketoisovalerate, which may be catalyzed, for example, by dihydroxyacid dehydratase;
  d) the α-ketoisovalerate from step c) to isobutyraldehyde, which may be catalyzed, for example, by a branched-chain α-keto acid decarboxylase; and,
  e) the isobutyraldehyde from step d) to isobutanol, which may be catalyzed, for example, by a branched-chain alcohol dehydrogenase.

In another embodiment, the isobutanol biosynthetic pathway comprises the following substrate to product conversions:
  a) pyruvate to acetolactate, which may be catalyzed, for example, by acetolactate synthase;
  b) the acetolactate from step a) to 2,3-dihydroxyisovalerate, which may be catalyzed, for example, by ketol-acid reductoisomerase;
  c) the 2,3-dihydroxyisovalerate from step b) to α-ketoisovalerate, which may be catalyzed, for example, by dihydroxyacid dehydratase;
  d) the α-ketoisovalerate from step c) to valine, which may be catalyzed, for example, by transaminase or valine dehydrogenase;
  e) the valine from step d) to isobutylamine, which may be catalyzed, for example, by valine decarboxylase;
  f) the isobutylamine from step e) to isobutyraldehyde, which may be catalyzed by, for example, omega transaminase; and,
  g) the isobutyraldehyde from step f) to isobutanol, which may be catalyzed, for example, by a branched-chain alcohol dehydrogenase.

In another embodiment, the isobutanol biosynthetic pathway comprises the following substrate to product conversions:
  a) pyruvate to acetolactate, which may be catalyzed, for example, by acetolactate synthase;
  b) the acetolactate from step a) to 2,3-dihydroxyisovalerate, which may be catalyzed, for example, by acetohydroxy acid reductoisomerase;
  c) the 2,3-dihydroxyisovalerate from step b) to α-ketoisovalerate, which may be catalyzed, for example, by acetohydroxy acid dehydratase;
  d) the α-ketoisovalerate from step c) to isobutyryl-CoA, which may be catalyzed, for example, by branched-chain keto acid dehydrogenase;
  e) the isobutyryl-CoA from step d) to isobutyraldehyde, which may be catalyzed, for example, by acylating aldehyde dehydrogenase; and,
  f) the isobutyraldehyde from step e) to isobutanol, which may be catalyzed, for example, by a branched-chain alcohol dehydrogenase.

Biosynthetic pathways for the production of 1-butanol that may be used include those described in U.S. Patent Application Publication No. 2008/0182308 and WO2007/041269. In one embodiment, the 1-butanol biosynthetic pathway comprises the following substrate to product conversions:
  a) acetyl-CoA to acetoacetyl-CoA, which may be catalyzed, for example, by acetyl-CoA acetyltransferase;
  b) the acetoacetyl-CoA from step a) to 3-hydroxybutyryl-CoA, which may be catalyzed, for example, by 3-hydroxybutyryl-CoA dehydrogenase;
  c) the 3-hydroxybutyryl-CoA from step b) to crotonyl-CoA, which may be catalyzed, for example, by crotonase;
  d) the crotonyl-CoA from step c) to butyryl-CoA, which may be catalyzed, for example, by butyryl-CoA dehydrogenase;
  e) the butyryl-CoA from step d) to butyraldehyde, which may be catalyzed, for example, by butyraldehyde dehydrogenase; and,
  f) the butyraldehyde from step e) to 1-butanol, which may be catalyzed, for example, by butanol dehydrogenase.

Biosynthetic pathways for the production of 2-butanol that may be used include those described by Donaldson et al. in U.S. Pat. No. 8,206,970; U.S. Patent Application Publication Nos. 2007/0292927 and 2009/0155870; International Publication Nos. WO 2007/130518 and WO 2007/130521. In one embodiment, the 2-butanol biosynthetic pathway comprises the following substrate to product conversions:
  a) pyruvate to alpha-acetolactate, which may be catalyzed, for example, by acetolactate synthase;
  b) the alpha-acetolactate from step a) to acetoin, which may be catalyzed, for example, by acetolactate decarboxylase;
  c) the acetoin from step b) to 3-amino-2-butanol, which may be catalyzed, for example, acetoin aminase;
  d) the 3-amino-2-butanol from step c) to 3-amino-2-butanol phosphate, which may be catalyzed, for example, by aminobutanol kinase;
  e) the 3-amino-2-butanol phosphate from step d) to 2-butanone, which may be catalyzed, for example, by aminobutanol phosphate phosphorylase; and,
  f) the 2-butanone from step e) to 2-butanol, which may be catalyzed, for example, by butanol dehydrogenase.

In another embodiment, the 2-butanol biosynthetic pathway comprises the following substrate to product conversions:
  a) pyruvate to alpha-acetolactate, which may be catalyzed, for example, by acetolactate synthase;
  b) the alpha-acetolactate from step a) to acetoin, which may be catalyzed, for example, by acetolactate decarboxylase;
  c) the acetoin to 2,3-butanediol from step b), which may be catalyzed, for example, by butanediol dehydrogenase;
  d) the 2,3-butanediol from step c) to 2-butanone, which may be catalyzed, for example, by dial dehydratase; and,
  e) the 2-butanone from step d) to 2-butanol, which may be catalyzed, for example, by butanol dehydrogenase.

Biosynthetic pathways for the production of 2-butanone that may be used include those described in U.S. Pat. No. 8,206,970 and U.S. Patent Application Publication Nos. 2007/0292927 and 2009/0155870. In one embodiment, the 2-butanone biosynthetic pathway comprises the following substrate to product conversions:
  a) pyruvate to alpha-acetolactate, which may be catalyzed, for example, by acetolactate synthase;
  b) the alpha-acetolactate from step a) to acetoin, which may be catalyzed, for example, by acetolactate decarboxylase;
  c) the acetoin from step b) to 3-amino-2-butanol, which may be catalyzed, for example, acetoin aminase;
  d) the 3-amino-2-butanol from step c) to 3-amino-2-butanol phosphate, which may be catalyzed, for example, by aminobutanol kinase; and,
  e) the 3-amino-2-butanol phosphate from step d) to 2-butanone, which may be catalyzed, for example, by aminobutanol phosphate phosphorylase.

In another embodiment, the 2-butanone biosynthetic pathway comprises the following substrate to product conversions:
  a) pyruvate to alpha-acetolactate, which may be catalyzed, for example, by acetolactate synthase;
  b) the alpha-acetolactate from step a) to acetoin which may be catalyzed, for example, by acetolactate decarboxylase;
  c) the acetoin from step b) to 2,3-butanediol, which may be catalyzed, for example, by butanediol dehydrogenase;
  d) the 2,3-butanediol from step c) to 2-butanone, which may be catalyzed, for example, by diol dehydratase.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, breadth and scope of the present application should not be limited by any of the above-described exemplary embodiments, but should be defined only in accordance with the claims and their equivalents.

EXAMPLES

Fermentation production of butanol may create a butanol based composition with less than 10% components, such as about ~7.6 wt % components, or less than 5% components. These components consist of primarily isobutyric acid and methylbutanol isomers with lesser levels of water, valeric acid, phenyl-ether alcohol and isobutyl isobutyrate. Trace concentrations (<100 ppm) of iso-butyraldehyde, ethanol, iso-butyl acetate, propan-1-ol, iso-amyl acetate, butan-1-ol, pentan-1-ol, acetoin and 2,3-butanediol also exist. The methods by which the samples are purified aim to reduce the isobutyric acid concentration to below 102 ppm.

Example 1

To determine the components of a butanol based composition produced during a fermentative process, 500 milliliters of two separate samples were obtained. The total concentration of the components of the butanol based compositions were estimated using a combination of calibrated and theoretical response factors for the components identified. The samples were analyzed by gas chromatography (GC) using flame ionization detection and a polar separation column. Results were calculated using an internal standard technique. A toluene internal standard was accurately added at a concentration of approximately 1000 ppm to aid quantification.

An HP6890 gas chromatograph with a flame ionization detector and electronic pressure control was set up with the following conditions.

TABLE 1

HP6890 gas chromatograph conditions.

| | |
|---|---|
| Column dimensions: | 50 m × 0.32 mm × 1.2 μm |
| Stationary phase: | CPWAX -52CB |
| Oven temperature: | 40° C./10 min/5° C./min/220° C./26 min |
| Injector type/Temperature | Split/160° C. |
| Detector type/Temperature: | FID/250° C. |
| Split ratio/Split flow: | 12:1/25.4 ml/min |
| Head pressure/Carrier gas: | 100 kPa Helium |
| EPC Mode/Program: | Ramped Pressure 14.5 psi/45 min/ 2.9 psi/min/21.75 psi/18.5 |
| Column Flow: | |
| Dead time/Velocity: | 30 cm/s |
| Make-up gas/Flow: | 45 ml/min Nitrogen |
| Hydrogen flow/Pressure: | 40 ml/min |
| Air flow/Pressure: | 450 ml/min |
| Sample size: | 1.0 μl |
| Injection technique: | Auto sampler |
| Data system method: | KRL |

TABLE 2

Retention time for components of butanol based composition.

| Component | R.T. (mins) | R.F. |
|---|---|---|
| iso-Butyraldehyde * | 7.80 | 0.4951 |
| Ethanol | 13.88 | 0.4550 |
| Iso-butyl Acetate | 18.06 | 0.6300 |
| 1-Propanol * | 19.10 | 0.5925 |
| Toluene I/S | 19.50 | 1.0000 |
| Methyl Propanol * | 22.10 | |
| i-Butyl-i-Butyrate | 22.30 | 0.6690 |
| i-Amyl Acetate | 23.20 | 0.5570 |
| N-Butanol | 23.70 | 0.6690 |
| i-Butyl-i-Valerate | 25.80 | 0.6690 |
| i-Pentyl i-Butyrate | 25.90 | 0.6690 |
| Methy Butanols * ** | 26.30 | 0.7210 |
| 1-Pentanol | 27.80 | 0.7240 |
| Hexyl Acetate * | 28.90 | 0.6565 |
| Acetoin * | 29.70 | 0.4380 |
| Hydroxy Hexanone | 36.16 | 0.6690 |
| i-Butyl Caprylate | 37.70 | 0.6690 |
| i-Butyric Acid * | 37.80 | 0.5096 |
| N-Butyric Acid | 39.97 | 0.5110 |
| i-Valeric Acid | 40.80 | 0.5110 |
| Phenyl Ethyl Alcohol | 47.20 | 0.7240 |
| Unknown | 52.00 | 0.7240 |

R.T. = retention time;
R.F. = response factor.
* Calibrated using gravimetric standards.
** Combined 3-methyl-1-butanol and 2-methyl-1-butanol.

The chromatographs for the two samples were very similar (see Table 3). The iso-butyraldehyde concentration increased slightly, but all the other components have remained constant within the limits of precision for the analysis.

TABLE 3

Component Concentrations.

| Component (% m/m) | Sample 1 | Sample 2 |
|---|---|---|
| Total Components | 7.6 | 7.6 |
| Water (by KF)* | 0.20 | 0.20 |
| Iso-Butyraldehyde* | 0.004 | 0.014 |
| Ethanol* | 0.004 | 0.005 |

TABLE 3-continued

Component Concentrations.

| Component (% m/m) | Sample 1 | Sample 2 |
|---|---|---|
| Iso-butyl Acetate | 0.004 | 0.004 |
| Propan-1-ol* | 0.012 | 0.012 |
| Iso-Butyl iso-Butyrate | 0.34 | 0.36 |
| Iso-Amyl Acetate | 0.004 | 0.004 |
| Butan-1-ol | 0.03 | 0.03 |
| Methyl Butanols* | 3.1 | 3.0 |
| Pentan-1-ol* | 0.003 | 0.004 |
| Acetoin* | 0.09 | 0.09 |
| Iso-Butyric Acid* | 3.3 | 3.3 |
| Iso-Valeric Acid | 0.14 | 0.14 |
| Phenyl Ethyl Alcohol | 0.25 | 0.25 |
| 2,3-Butanediol* | 0.04 | 0.05 |

*Calibrated Component

Example 2

To remove the components from the butanol (i-BuOH), the organic is reacted with excess CaO (lime) before filtering and distilling the mixture. At a small scale 604 g butanol feed mix (~18 g butyric acid, 0.20 mol) was added to a beaker followed by 104 g CaO (1.85 mol, 8 times excess with respect to butyric acid) and left to stir overnight (approximately 12 hours) with a foil cover over the beaker. The suspension was then filtered through a sintered buchner funnel to remove the residual solid and 465 g of liquid were collected. The liquid was then loaded into a 2 L glass reboiler containing anti-bumping granules, purged with nitrogen and heated to 110° C. using an electric mantle. The reactor was fitted with a lagged glass distillation column consisting of 14 trays; 7 theoretical stages. A double jacketed-cold finger condenser was used to provide adequate reflux as material was collected overhead. An initial yellow fraction was collected between 90-108° C. (10 g) before i-BuOH was collected at 109-110° C. The vapor temperature in the reboiler during collection of the i-BuOH fraction was also 110° C. After the i-BuOH fraction had been collected (267 g, 51% yield with respect to the initial feed mixture) the temperature in the reboiler rose to 120° C. whilst the temperature overhead remained at 110° C. A second fraction of i-BuOH was therefore collected at the required specification (56 g, 10%).

Example 3

To remove isobutyric acid from an isobutanol composition (3.1 wt % isobutyric acid, 96.9 wt % isobutanol), 64.8 g of the isobutanol composition was added to a separating funnel with 200 ml of 0.47 M $K_2CO_3$ aqueous solution (4.1 fold molar excess $K_2CO_3$ to isobutyric acid). The mixture was well mixed with occasional venting and left to separate for two hours. The organic layer was collected (49.8 g, 79.3%) and analyzed by GC to show an isobutyric acid content of <100 ppm mass/mass (m/m).

Example 4

To remove isobutyric acid from an isobutanol composition (2.4 wt % isobutyric acid, 97.6 wt % isobutanol), 9 g of Amberlyst-26-(OH) resin was loaded into a glass tube reactor before being soaked in synthetic isobutanol. The resin was washed with 50 ml of synthetic isobutanol at a flow rate of 4 ml/min at 20° C. The isobutanol composition was then passed up-flow over the resin using an HPLC pump at a flow rate of 0.5 ml/min at 20° C., and the product was collected as fractions and analyzed by GC. The concentration of isobutyric acid found in the collected material was below 0.01 wt % after approximately 30 g of isobutanol composition had passed over the resin.

Example 5

To remove isobutyric acid and acetoin from a bio-isobutanol composition (3.3 wt % isobutyric acid, 0.09 wt % acetoin, and 96.6% isobutanol), 51.1 g of the bio-isobutanol composition containing isobutyric acid and acetoin was added to a round bottom flask with 6.8 g of calcium hydroxide. This mixture was stirred overnight at room temperature and a sample was taken for GC analysis. The isobutyric acid content of the sample was less than 0.01 wt % and the acetoin concentration was less than 0.01 wt %.

Example 6

Prophetic

An alternative to reaction with CaO is to react the butanol mixture with aqueous alkali material to produce isobutyrate salts, which can be separated from the mixture. By way of an example, in a first reaction mechanism, isobutyric acid is removed from solution via a reaction with sodium hydroxide which creates sodium isobutyrate and water. By way of another example, in a second reaction mechanism, isobutyric acid is reacted with sodium carbonate producing sodium isobutyrate and sodium formate ($NaHCO_3$). Additionally, the second reaction mechanism evolves $CO_2$ as a byproduct leading to a pressure increase.

In both mechanisms, a sample of a synthetic butanol mixture consisting of 97% butanol with 3% isobutyric acid is prepared and the concentration is measured via gas chromatography (GC) to confirm the composition components. The mixture is then added to a beaker, and a 2M sample of the reactant (either NaOH or $Na_2CO_3$) is added to the beaker. The mixture is continuously stirred, and to confirm the reaction has reached completion, the pH of the aqueous phase is tested. Water may be added to an aliquot of the reaction mass to create an aqueous phase, if one does not exist. A pH greater than 7 confirms that the reaction has reached completion.

The product reaction mass is tested for composition using GC to determine the concentrations of butanol, isobutyric acid and sodium isobutyrate (g/L). Total acids concentration is measured using back titration by adding excess $Na_2CO_3$ (aq) to titrate the acids and then titrating the residual carbonate with dilute HCl. Bench scale fractional distillation is used to recover the final product. Distillate and aqueous phase samples are collected from the batch fractional distillation and analyzed via GC for concentrations of butanol, isobutyric acid and sodium isobutyrate. The isobutyric acid concentration in the butanol product (organic phase) should be less than 102 ppm.

Example 7

Prophetic

An additional method of purifying butanol utilizes an anion exchange resin. In a batch experiment, the anion-exchange resin is added to a butanol sample containing isobutyric acid. The acid is removed by the resin, and the solid and liquid phases are then separated by filtration. A sampled of 97% butanol and 3% isobutyric acid is prepared in the lab and the composition is confirmed using GC analysis. The pH of the solution is recorded. Separately, the anion-exchange resin is charged by mixing the resin, Dowex-22, with 0.1M NaOH solution in a stirred flask for 2 hours. The resin is water washed to remove residual NaOH until the pH reached 7.0. The resin is then filtered until light vacuum and added to a small volume of methanol to prevent drying. In a continuously stirred flask, resin is slowly added to the butanol mixture until the pH of the solution reached 7.0, marking the completion of the separation. The mass is then mechanically filtered to separate the solids from the liquid. The concentrations of butanol and isobutyric acid in the liquid phase are then determined using GC analysis. Isobutyric acid content should be less than 102 ppm in the final butanol product. The total acids are then collected from the solids fraction by rinsing the solids with three volumes of methanol and stirring in a 0.1M NaOH solution for 2 hours. The solids mixture is then filtered, and the filtrate is evaporated leaving behind the organic acid sodium salts. These salts are analyzed for total acids.

What is claimed:

1. A method for removing isobutyric acid from a butanol based composition, the method comprising:
   (a) providing a butanol based composition comprising isobutyric acid;
   (b) contacting the butanol based composition with an excess level of a base;
   (c) passing the composition through a filtration system; and
   (d) passing the filtered composition through a distillation system.

2. The method of claim 1, wherein the base is selected from the group consisting of calcium oxide, calcium hydroxide, sodium hydroxide, sodium carbonate, sodium phosphate, sodium ethoxide, potassium hydroxide, potassium carbonate, potassium phosphate, magnesium hydroxide, ammonium hydroxide, and combinations thereof.

3. The method of claim 2, wherein the base is calcium oxide.

4. The method of claim 1, wherein contacting the butanol based composition with a base results in precipitation of a salt.

5. The method of claim 1, wherein the filtration system comprises equipment selected from the group consisting of a funnel with a porous barrier, a sinter funnel, a vacuum filtration unit, a centrifugation unit, and combinations thereof.

6. The method of claim 1, wherein the distillation system comprises a distillation unit.

7. The method of claim 6, wherein the distillation unit is a batch distillation unit or a continuous distillation unit.

8. The method of claim 6, wherein the distillation unit comprises a distillation column, a heating unit, and a condenser.

9. The method of claim 1, wherein one or more fractions comprising purified butanol are removed from the distillation system.

10. The method of claim 1, wherein the butanol based composition is produced by a genetically modified organism.

* * * * *